United States Patent [19]
Werenicz et al.

[11] Patent Number: 6,120,887
[45] Date of Patent: Sep. 19, 2000

[54] DISPOSABLE ARTICLES HAVING A CONTINUOUS THERMOPLASTIC COATING COMPRISING A METALLOCENE POLYOLEFIN

[75] Inventors: Harald Werenicz, Reppenstedt; Thomas Wittkopf, Adendorf; Gerhard Voss, Lüneburg; Peter Remmers, Hamburg, all of Germany; Mark G. Katsaros, Mahtomedi, Minn.; Robert G. Polance, II, Vadnais Heights, Minn.; Mark S. Kroll, Arden Hills, Minn.; Wendy Hoenig; Selim Yalvac, both of Lake Jackson, Tex.; Kalyan Sehanobish, Friendswood, Tex.; Teresa Karjala; Deepak Parikh, both of Lake Jackson, Tex.; David C. Kelley, Angleton, Tex.

[73] Assignee: H. B. Fuller Licensing & Financing, Inc., St. Paul, Minn.

[21] Appl. No.: 08/705,380

[22] Filed: Aug. 29, 1996

Related U.S. Application Data

[63] Continuation-in-part of application No. PCT/EP96/00377, Jan. 30, 1996, and a continuation-in-part of application No. PCT/EP95/00665, Feb. 23, 1995, abandoned.

[51] Int. Cl.[7] ............................. B32B 27/32; A61F 13/15
[52] U.S. Cl. ........................ 428/219; 428/131; 428/500; 428/515; 428/516; 604/366; 604/370; 604/372; 524/570; 524/579; 156/334
[58] Field of Search ................................. 604/366, 370, 604/372; 428/500, 515, 131, 219, 516; 524/570, 579; 156/334

[56] References Cited

U.S. PATENT DOCUMENTS

| | | |
|---|---|---|
| 4,627,847 | 12/1986 | Puletti et al. . |
| 4,692,161 | 9/1987 | Puletti et al. . |
| 4,728,325 | 3/1988 | Spiller .................................. 604/372 |
| 4,798,602 | 1/1989 | Laus ....................................... 604/372 |
| 5,376,439 | 12/1994 | Lodgson et al. .................... 604/370 X |
| 5,422,172 | 6/1995 | Wu . |

FOREIGN PATENT DOCUMENTS

| | | |
|---|---|---|
| 0 187 728 A2 | 7/1986 | European Pat. Off. . |
| 0 189 911 A3 | 8/1986 | European Pat. Off. . |
| 0 295 694 | 12/1988 | European Pat. Off. . |
| 0 295 694 A2 | 12/1988 | European Pat. Off. . |
| 0 295 694 A3 | 12/1988 | European Pat. Off. . |
| 0 395 381 A3 | 10/1990 | European Pat. Off. . |
| 0 508 485 A1 | 10/1992 | European Pat. Off. . |
| 0 456 885 B1 | 2/1995 | European Pat. Off. . |
| 2 583 338 | 12/1986 | France . |
| 38 36 434 A1 | 8/1988 | Germany . |
| 96322880 | 6/1995 | Japan . |
| 96323930 | 3/1997 | Japan . |
| WO 96/26697 | 9/1996 | WIPO . |

OTHER PUBLICATIONS

Index '93, Int. Congress for the Nonwovens and Disposable Industries (see search report).

*Primary Examiner*—Fred Teskin
*Attorney, Agent, or Firm*—Nancy N. Quan; Carolyn A. Fischer

[57] ABSTRACT

This invention relates to a non-contact coating method for producing a continuous coating and articles constructed therefrom. This invention further relates to a method for producing a textile material with a moisture-impermeable barrier layer and to a method for producing a moisture-absorbing article of hygiene which has such a barrier layer. This invention particularly relates to a textile material and hygienic disposable articles comprising a body fluid impermeable barrier layer which can be produced from a non-contact coating method. Preferably, the thermoplastic composition used for producing the barrier layer exhibits certain rheological characteristics and comprises at least one homogeneous linear or substantially linear interpolymer of ethylene with at least one $C_3$–$C_{20}$ alpha-olefin, further characterized by each said interpolymer having a polydispersity less than about 2.5.

25 Claims, 1 Drawing Sheet

DISPOSABLE ARTICLES HAVING A CONTINUOUS THERMOPLASTIC COATING COMPRISING A METALLOCENE POLYOLEFIN

REFERENCES TO RELATED APPLICATIONS

This application is a continuation-in-part of application Ser. Nos. PCT/EP96/00377, filed Jan. 30, 1996 and PCT/EP95/00665, filed Feb. 23, 1995, abandoned.

FIELD OF THE INVENTION

This invention relates to a non-contact coating method for producing a continuous coating and articles constructed therefrom. This invention further relates to a method for producing a textile material with a moisture-impermeable barrier layer and to a method for producing a moisture-absorbing article of hygiene which has such a barrier layer. This invention particularly relates to a textile material and hygienic disposable articles comprising a body fluid impermeable barrier layer which can be produced from a non-contact coating method. Preferably, the thermoplastic composition used for producing the barrier layer exhibits certain rheological characteristics and comprises at least one homogeneous linear or substantially linear interpolymer of ethylene with at least one $C_3$–$C_{20}$ alpha-olefin, further characterized by each said interpolymer having a polydispersity less than about 2.5.

BACKGROUND OF THE INVENTION

For various applications, materials are required which are impermeable to liquids such as water and body fluids, but at the same time have a textile character which is as close as possible to materials without the impermeability characteristics. One example of such application is hygienic articles such as disposable diapers, feminine napkins, panty liners, surgical drapes, bed pads, and the like. Such hygienic articles often have a substantial absorption capacity. To ensure that the liquid which is to be absorbed does not reach articles of clothing, such hygienic articles customarily have a continuous layer of a body fluid impermeable film on their garment facing side. Since touching this film material is an unwelcome sensation for a number of users, it has been suggested to cover the outward side of the film with a thin layer of textile material so that the article has a textile feel also on its exterior surface.

EP-A-O 187 728 teaches a disposable diaper with a barrier layer in the form of a plastics material film, typically consisting of a polyolefin, a polyacrylate, of PVC, nylon or other thermoplastic material. The barrier film is laminated, adhered or welded onto a thin nonwoven layer, which makes it necessary to prepare the film laminate off-line. As an alternative, it is suggested that the plastics material of the film is to be extrusion coated onto the nonwoven. The laminate, thus formed, is then used as the outermost material layer in such a way that the film layer is on the inside, so that the outer nonwoven layer provides the desired exterior texture. This production method is rather expensive. High molecular weight plastic materials such as polyethylene, polypropylene, polyacrylate and so on, have low melt flow indices and can (if at all) only be processed into impermeable films on very sophisticated machinery. Separately producing the film, with subsequent laminating onto the nonwoven, is even more inefficacious in view of the additional production step required.

U.S. Pat. No. 5,422,172 teaches an elastic laminated sheet of an incrementally stretched nonwoven fibrous web and an elastomeric film, as well as a method for making the same. The elastic film may comprise a polyolefin produced by a reaction conducted in the presence of a single site catalyst. The elastic film may be directly extruded from a die separated from the nonwoven substrates in such a manner that the resultant elastic film is applied to a nonwoven layer or interposed between two nonwoven layers. U.S. Pat. No. 5,422,172 only discloses the use of elevated application temperatures, i.e., in the range of 500° F. to 625° F.

U.S. Pat. Nos. 4,692,161 and 4,627,847 teach a leakage waste barrier for the edge of an absorbent hygienic article provided by coating a hot melt adhesive onto the edge area of a nonwoven sheet material. Depending on the actual type of application, this hot melt adhesive can also serve a constructive function, in combination with its function as a barrier, in that it can adhere the nonwoven to other materials of the hygienic article. The hot melt is to be coated in a conventional manner by slot nozzle coating, transfer coating, spray coating or other such methods. The above-mentioned U.S. patents indicate that the hot melt coating must have a minimum thickness of 25 mm, preferably at least 75 mm, so that a continuous closed barrier layer is achieved.

Conventional slot nozzle coatings on uneven substrates such as nonwovens are typically done by keeping the slot nozzle in permanent contact with the substrate such that the nozzle lies on the substrate during the coating. It is unproblematic to coat hot melt adhesives onto uneven substrates with slot nozzles or spray coating methods, provided that only a discontinuous coating is required such as for constructive applications wherein the coating weight of the hot melt ranges from about 3 g/m$^2$ to about 10 g/m$^2$. If, however, a continuous layer is to be created, this can only be done using these customary coating methods if the coating weight of the hot melt is greater than about 30 g/m$^2$.

Such high coating weights are expensive. Furthermore, direct coating with a slot nozzle provides substantial mechanical and thermal stresses on the coated substrates, especially since the slot nozzle is heated during coating. Therefore, very sensitive substrates such as nonwovens made of very fine or low melting point fibers can not always be coated with hot melt from a slot nozzle in a customary manner without damaging the substrate. Such problems can not be overcome when coating with heated coating rollers or spray coating with heated airstreams. The high coating weights of this prior art lead to increased stiffness of the coated substrate, thus impairing the textile character.

Similar problems occur in the production of hygienic articles and in other areas, such as fabric production, wherein the resulting materials are required to exhibit liquid impermeability, especially body fluid impermeability, with textile character which is as unimpaired as possible. This is especially pertinent for improving the comfort of the user. Presently, in such technical fields, production methods utilizing preformed laminated films are preferred.

Therefore, there remains a need for a non-contact, low temperature method capable of producing a continuous coating layer having low coating weights.

SUMMARY OF THE INVENTION

The applicants have found a coating method that overcomes the aforementioned problems. The coating method employs a noncontact application wherein a thermoplastic composition is thermally made flowable and released from a coating device onto a substrate. The thermoplastic composition is thus coated onto the substrate without contact between said coating device and said substrate. Preferably, a liquid-impermeable, especially a body fluid impermeable, barrier wherein the textile character is not substantially impaired is produced. Since the method employs low coating weights of the thermoplastic composition, it eliminates the economic disadvantages of current methods as well as improves the tactile quality of the resulting article. Additionally, the method is suitable for coating a variety of heat sensitive materials. Preferably, the substrate is a "textile material" which in the context of this invention means not only a woven material made of yarn, but also any material made from fibers such as nonwoven, as well as nonwoven composites and the like, which materials play a major role in the area of hygienic article production. Since the coating device and substrate do not contact each other, the mechanical stresses on the substrate are much less than prior art methods. For heat sensitive substrate, the thermoplastic composition is preferably coated at temperatures of less than about 160° C., more preferably less than 125° C., most preferably less than 110° C., to reduce the heat-induced stresses on the substrates being coated. This is advantageous for coating and mutually bonding thermally sensitive substrates.

The thermoplastic composition preferably exhibits certain rheological characteristics such that the complex viscosity at high shear rates (1,000 rad/sec) is less than about 500 poise and the complex viscosity at low shear rates (1 rad/sec) is between about 100 and about 1,000 poise, with the complex viscosity being measured in accordance with the procedure for "Rheological Testing" set forth below. Some neat thermoplastic resins, such as typical film grade polyolefins, may be suitable for the method of the present invention. However, compounded hot melt adhesives are preferred due to the ability to independently control the visco-elastic properties, open time, etc. Compounded hot melt are also advantageous to insure adequate adhesion to the carrier substrate or for a more controllable open and close time of the coating.

The resulting coating produced from said method is useful for a variety of applications wherein a consistent continuous coating is desired. Coating weights of less than 30 g/m$^2$ of the thermoplastic composition are preferred to reduce expenditure and improve the tactile quality of disposable hygienic articles. However, coating weights higher than 30 g/m$^2$ may be useful for other applications, such as medical drapes, or wherein reducing the mechanical and heat-induced stresses is of primary importance.

The resulting coating is preferable for producing a body fluid impermeable barrier layer in a disposable hygienic article having improved exterior tactile quality. The coating method is particularly advantageous for manufacturing as it employs fewer production steps than prior art coating methods. Improving productivity as well as reducing the coating weight mass per area results in coatings and corresponding articles that are less expensive than prior art.

The disposable article comprises at least one permeable substrate layer and at least one fluid impermeable barrier layer substantially adhered to the permeable substrate layer on at least one face, wherein the barrier layer comprises a thermoplastic composition coated as a continuous film at an area weight of less than 30 g/m$^2$. The permeable substrate is preferably a nonwoven web. However, paper, durable fabric, as well as any other material available as web may be coated with this coating method. The permeable substrate may contribute significantly to the overall strength and integrity of the lamination. Preferably, the substrate exhibits sufficient strength such that it can not be torn easily by hand in either machine direction or in cross-direction.

Furthermore, the applicants have found that certain thermoplastic compositions are especially preferred for producing a continuous coating. The present invention is a continuous coating comprising from about 10 wt-% to as much as 100% of at least one homogeneous linear or substantially linear interpolymer of ethylene with at least one $C_3$–$C_{20}$ alpha-olefin, further characterized by each said interpolymer having a polydispersity less than about 2.5 and up to 90 wt-% of at least one viscosity reducing agent selected from the group consisting of tackifier, wax, plasticizer, oils and mixtures thereof. Preferably, the thermoplastic composition comprises up to 65 wt-% of at least one tackifier and up to 40 wt-% of at least one wax. Additionally, the thermoplastic composition may also comprise up to 65 wt-% of a plasticizer selected from the group consisting of oils, cyclohexane dimethanol dibenzoate compounds, liquid elastomers, liquid resins, and mixtures thereof.

DETAILED DESCRIPTION OF THE DRAWING

Figure 1:
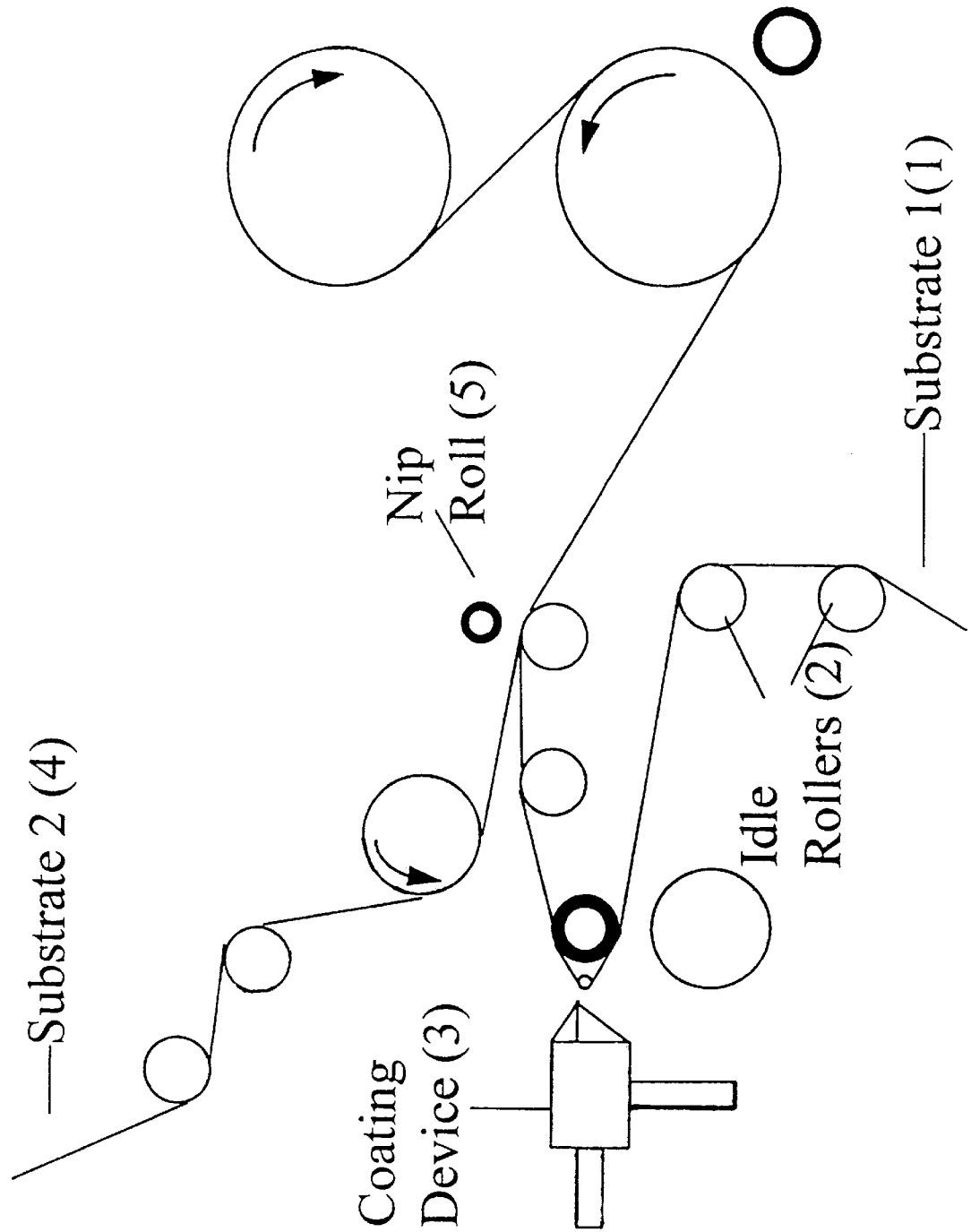
FIG. 1 depicts a preferred method for coating the thermoplastic compositions of the present invention wherein a continuous thermoplastic coating is formed and adhered to a carrier substrate.

Substrate 1 (1) is advanced by the drive rolls (6) past a series of idle rollers (2) to ensure the web is in proper alignment prior to approaching the coating device (3). The coating device is located at a distance most often ranging from about 0.5 mm to about 20 mm, depending on the properties of the thermoplastic composition being coated. Substrate 2 (4) is optionally adhered to the coating surface by means of a nip roll (5). When adherence to a second substrate is intended, it is often preferred to position the nip roll closer to the coating device at a distance of about 25 cm from the coating device. In the preferred embodiment, Substrate 2 may be any substrate present in a hygienic article such as an absorbent, elastomeric strands or webs, tissue, films, coverstock materials such as nonwoven or perforated polyethylene, as well as any material that is not necessarily in the form of a web such as superabsorbent polymer.

DETAILED DESCRIPTION OF THE INVENTION

In the preferred method of coating the thermoplastic composition of the present invention, a melted hot melt adhesive, preferably substantially air-free, is released from a coating or release device in such a way that it exits the device as a continuous film. A typical example for this is a slot nozzle, as it has previously been used for coating in direct contact with a substrate. Thus, melt coating devices which are already at hand can be reset for use according to the invention in that the slot nozzle is lifted off the substrate and is adjusted to have a suitable distance from the substrate.

When the viscous but flowable molten adhesive leaves the coating device, it does not contact the substrate immediately, but rather travels for a distance as a continuous coating film suspended above the substrate without touching either the device or the substrate. The distance between the coating device and the substrate ranges from about 0.5 mm to about 20 mm. It is possible that at suitable machine speed settings, and with specific adhesives or other coating materials, the distance can be even greater than 20 mm. The distance is largely dictated by the viscosity, flow properties such as shear thing behavior, line speed and open time of the thermoplastic composition being coated. It is surmised that the thermoplastic composition builds in viscosity and cohesive strength to the extent that any filaments or fibers present on the substrate surface cannot penetrate the coating, yet the thermoplastic composition is molten or soft enough to adequately adhere to the substrate.

It has been shown to be especially advantageous, that the coating later contacts the substrate in a substantially horizontal direction rather than in a vertical direction. To realize this advantage, a roller can be provided in the path of movement of the substrate to give the substrate a substantially vertical, upward direction, as the substrate passes the coating device. Additionally, the coating device, such as a slot nozzle, can be provided substantially horizontally beside the roller so that the coating travels from the side towards the surface of the substrate.

The diameter of the coating role is preferably about 15 mm to about 50 mm in diameter with the nozzle above the center of the coating roll such that the angle at which the thermoplastic coating contacts the substrate is less than about 60° C. as the substrate is moving away from the nozzle. The coating head is adjusted by one of ordinary skill in the art to optimize for even flow and distribution of the thermoplastic coating over the entire width of the application.

Thereafter, the sufficiently viscous coating contacts the substrate surface and adheres to the surface without deeply penetrating into the substrate. Particularly for coating thermoplastic compositions that are relatively tack free upon cooling, there is a distinct interface between the coating and the substrate which is evident by the ability to remove the coating as a continuous film from the substrate. This interface is also present when a tacky thermoplastic composition is employed. However, in this instance since the coating and substrate are inseparable, the interface is less evident. When the substrate is preferably a textile material such as a nonwoven, the thus produced material comprises the textile substrate layer and a coating, preferably a hot melt barrier layer. If the thermoplastic coating is of such a composition that it substantially detackifies after sufficient cooling, the laminate of the coated substrate, thus formed, can be rolled up and stored. The laminate can then be used at some later time, e.g., as a body fluid impermeable backsheet having improved tactile quality in a disposable hygienic article. The laminate can be bonded by any suitable bonding technique including ultrasonic bonding, heat welding, or more commonly adhesive bonding.

Preferably, the coating of the barrier layer is done inline immediately before any further processing of the thus produced coated textile laminate. In such a case, the surface of the barrier layer which is pointing away from the substrate and is still sufficiently tacky can be used for a constructive adhesion step and therefore can also serve to bond the coated textile material to other elements of a hygienic article. Other elements that could be simultaneously bonded in this manner during the formation of the barrier layer include absorbent, superabsorbent polymer, elastomeric strands or webs, tissue, films, as well as various permeable coverstock materials such as nonwoven or perforated films. This method has found to be particularly advantageous for bonding porous webs including hook and loop fastening webs such as Velcro®.

Since the hot melt coating can be provided at extremely low temperatures, materials can also be provided with barrier layers which are too sensitive mechanically and/or thermally for customary coating methods. Such sensitive materials include low gauge polyethylene materials, low basis weight nonwovens and the like. A substantial advantage of the invention is that continuous, sufficiently impermeable barrier layers can be made from hot melts at very low coating weights. Even with customary commercially available hot melts, closed barrier layers can be produced at coating weight of not more than 30 g/m$^2$, and generally, it is easily possible to achieve coating weights between 10 g/m$^2$ and 20 g/m$^2$ and most preferably less than 10 g/m$^2$. As previously stated, the prior art coating of hot melts according to customary methods for forming edge leakage barriers, as in U.S. Pat. No. 4,692,161, requires area weights of about 70 g/m$^2$ to create the preferred film thickness of around 75 mm. At a thickness of 25 mm, the suggested minimum according to this art, the contact-coated layer is perforated by substrate fiber, and is not closed.

The very thin barrier layers which can be produced according to the invention not only contribute to the economical advantages of the inventive method, but also make it possible to achieve a very much reduced stiffness of the material, which thus comes much closer, in its properties, to a textile material which is not provided with a barrier layer at all.

THE THERMOPLASTIC COMPOSITION

As previously mentioned, uncompounded thermoplastic materials such as polyolefins, especially polyethylene, polypropylene, amorphous polyolefins such as Vestoplast 703® (Hüls) and the like, may be suitable thermoplastic materials for the coating method of the present invention.

A preferred polyolefin, typically described as "metallocene polyolefins", are produced with a single-site catalyst resulting in a homogeneous distribution of comonomer branching, and a narrow molecular weight distribution, i.e., a molecular weight distribution, $M_w/M_n$, less than or equal to 3, preferably less than or equal to 2.5. The connotation "metallocene" is not meant in any way to be limiting regarding the specific catalyst used in the process of manufacturing the copolymer but merely an abbreviated description of the homogeneously branched linear or substantially linear polymer structures themselves.

By the term homogenous, it is meant that any comonomer is randomly distributed within a given interpolymer molecule and substantially all of the interpolymer molecules have the same ethylene/comonomer ratio within that interpolymer. The DSC melting peak of homogeneous linear and substantially linear ethylene polymers will broaden as the density decreases and/or as the number average molecular weight decreases. However, unlike heterogeneous polymers, when a homogeneous polymer has a melting peak greater than 115° C. (such as is the case of polymers having a density greater than 0.940 g/cm$^3$), such polymers do not additionally have a distinct lower temperature melting peak.

In addition or in the alternative, the homogeneity of the polymers is typically described by the SCBDI (Short Chain Branch Distribution Index) or CDBI (Composition Distribution Branch Index) and is defined as the weight percent of the polymer molecules having a comonomer content within 50 percent of the median total molar comonomer content. The SCBDI of a polymer is readily calculated from data obtained from techniques known in the art, such as, for example, temperature rising elution fractionation (abbreviated herein as "TREF") as described, for example, in Wild et al, Journal of Polymer Science, Poly. Phys. Ed., Vol. 20, p. 441 (1982), in U.S. Pat. Nos. 4,798,081 (Hazlitt et al.), or in 5,089,321 (Chum et al.) the disclosures of all of which are incorporated herein by reference. The SCBDI or CDBI for the homogeneous linear and for the substantially linear ethylene/α-olefin polymers used in the present invention is preferably greater than 50 percent.

Heterogenous polymers are ethylene/α-olefin interpolymers characterized as having a linear backbone and a DSC melting curve having a distinct melting peak greater than 115° C. attributable to a high density fraction. Heterogeneous interpolymers will typically have an $M_w/M_n$ greater than 3 (when the density of the interpolymer is less than about 0.960 g/cc) and will typically have a CDBI less than or equal to 50, indicating that such interpolymers are a mixture of molecules having differing comonomer contents and differing amounts of short chain branching.

The homogeneous polyethylenes useful in this invention fall into two broad categories, the linear homogeneous polyethylenes and the substantially linear polyethylenes. Both are known.

Homogeneous linear ethylene polymers have long been commercially available. As exemplified in U.S. Pat. No. 3,645,992 to Elston, homogeneous linear ethylene polymers can be prepared in conventional polymerization processes using Ziegler-type catalysts such as, for example, zirconium and vanadium catalyst systems. U.S. Pat. Nos. 4,937,299 to Ewen et al. and 5,218,071 to Tsutsui et al. disclose the use of metallocene catalysts, such as catalyst systems based on hafnium, for the preparation of homogeneous linear ethylene polymers. Homogeneous linear ethylene polymers are typically characterized as having a molecular weight distribution, $M_w/M_n$, of about 2. Commercially available examples of homogeneous linear ethylene polymers include those sold by Mitsui Petrochemical Industries as Tafmer™ resins and by Exxon Chemical Company as Exact™ resins.

The substantially linear ethylene polymers (SLEPs) are homogeneous polymers having long chain branching. They are disclosed in U.S. Pat. Nos. 5,272,236 and 5,272,272, the disclosures of which are incorporated herein by reference. SLEPs are available from The Dow Chemical Company as polymers made by the Insite™ Process and Catalyst Technology, such as Affinity™ polyolefin plastomers (POPs). SLEPs can be prepared via the solution, slurry, or gas phase, preferably solution phase, polymerization of ethylene and one or more optional α-olefin comonomers in the presence of a constrained geometry catalyst, such as is disclosed in European Patent Application 416,815-A, incorporated herein by reference. The constrained geometry catalysts are described in more detail later.

The term "substantially linear" means that, in addition to the short chain branches attributable to homogeneous comonomer incorporation, the ethylene polymer is further characterized as having long chain branches in that the polymer backbone is substituted with an average of 0.01 to 3 long chain branches/1000 carbons. Preferred substantially linear polymers for use in the invention are substituted with from 0.01 long chain branch/1000 carbons to 1 long chain branch/1000 carbons, and more preferably from 0.05 long chain branch/1000 carbons to 1 long chain branch/1000 carbons. In contrast to the term "substantially linear", the term "linear" means that the polymer lacks measurable or demonstrable long chain branches, i.e., the polymer is substituted with an average of less than 0.01 long chain branch/1000 carbons.

For ethylene/α-olefin interpolymers, the long chain branch is longer than the short chain branch that results from the incorporation of the α-olefin(s) into the polymer backbone. Each long chain branch has the same comonomer distribution as the polymer backbone and can be as long as the polymer backbone to which it is attached.

The presence of long chain branching can be determined in ethylene polymers by using $^{13}C$ nuclear magnetic resonance (NMR) spectroscopy and is quantified using the method described by Randall (Rev. Macromol. Chem. Phys., C.29, V. 2&3, p. 285–297), the disclosure of which is incorporated herein by reference.

As a practical matter, current $^{13}C$ nuclear magnetic resonance spectroscopy cannot determine the length of a long chain branch in excess of six carbon atoms. However, there are other known techniques useful for determining the presence of long chain branches in ethylene polymers, including ethylene/1-octene interpolymers. Two such methods are gel permeation chromatography coupled with a low angle laser light scattering detector (GPC-LALLS) and gel permeation chromatography coupled with a differential viscometer detector (GPC-DV). The use of these techniques for long chain branch detection and the underlying theories have been well documented in the literature. See, e.g., Zimm, G. H. and Stockmayer, W. H., J. Chem. Phys., 17,1301 (1949) and Rudin, A., *Modern Methods of Polymer Characterization,* John Wiley & Sons, New York (1991) pp. 103–112, both of which are incorporated by reference. Further, in and particular, A. Willem deGroot and P. Steve Chum, both of The Dow Chemical Company, at the Oct. 4, 1994 conference of the Federation of Analytical Chemistry and Spectroscopy Society (FACSS) in St. Louis, Mo., presented data demonstrating that GPC-DV is a useful technique for quantifying the presence of long chain branches in substantially linear ethylene polymers.

The empirical effect of the presence of long chain branching in the substantial linear ethylene/α-olefin interpolymers used in the invention is manifested as enhanced rheological properties which are quantified and expressed herein in terms of gas extrusion rheometry (GER) results and/or a melt flow, $I_{10}/I_2$, which may be varied independently of the $M_w/M_n$.

Substantially linear ethylene polymers are further characterized as having:

(a) a melt flow ratio, $I_{10}/I_2 \geq 5.63$, (b) a molecular weight distribution, $M_w/M_n$ as determined by gel permeation chromatography and defined by the equation:

$$(M_w/M_n) \leq (I_{10}/I_2) - 4.63,$$

(c) a critical shear stress at the onset of gross melt fracture, as determined by gas extrusion rheometry, of greater than $4 \times 10^6$ dynes/cm² or a gas extrusion rheology such that the critical shear rate at onset of surface melt fracture for the substantially linear ethylene polymer is at least 50 percent greater than the critical shear rate at the onset of surface melt fracture for a linear ethylene polymer, wherein the substantially linear ethylene polymer and the linear ethylene polymer comprise the same comonomer or comonomers, the linear ethylene polymer has an $I_2$, $M_w/M_n$ and density within ten percent of substantially linear ethylene polymer and wherein the respective critical shear rates of the SLEP and the linear ethylene polymer are measured at the same melt temperature using a gas extrusion rheometer, and (d) a single differential scanning calorimetry, DSC, melting peak between –30 and 150 C.

An apparent shear stress versus apparent shear rate plot is used to identify the melt fracture phenomena and quantify the critical shear rate and critical shear stress of ethylene polymers. According to Ramamurthy in the Journal of Rheology, 30(2), 337–357, 1986, the disclosure of which is incorporated herein by reference, above a certain critical flow rate, the observed extrudate irregularities may be broadly classified into two main types: surface melt fracture and gross melt fracture.

Surface melt fracture occurs under apparently steady flow conditions and ranges in detail from loss of specular film gloss to the more severe form of "sharkskin." Herein, as determined using the above-described GER, the onset of surface melt fracture (OSMF) is characterized at the beginning of losing extrudate gloss at which the surface roughness of the extrudate can only be detected by 40× magnification. The critical shear rate at the onset of surface melt fracture for the substantially linear ethylene polymers is at least 50 percent greater than the critical shear rate at the onset of surface melt fracture of a linear ethylene polymer having essentially the same $I_2$ and $M_w/M_n$.

Gross melt fracture occurs at unsteady extrusion flow conditions and ranges in detail from regular (alternating rough and smooth, helical, etc.) to random distortions. For commercial acceptability to maximize the performance properties of films, coatings and moldings, surface defects should be minimal, if not absent. The critical shear stress at the onset of gross melt fracture for the substantially linear ethylene polymers, especially those having a density >0.910 g/cc, used in the invention is greater than $4\times10^6$ dynes/cm$^2$. The critical shear rate at the onset of surface melt fracture (OSMF) and the onset of gross melt fracture (OGMF) will be used herein based on the changes of surface roughness and configurations of the extrudates extruded by a GER. Preferably, the substantially linear ethylene polymer will be characterized by its critical shear rate when used as the first ethylene polymer of the invention and by its critical shear stress when used as the second ethylene polymer of the invention.

Determination of the critical shear rate and critical shear stress in regards to melt fracture as well as other rheology properties such as rheological processing index (PI), is performed using a gas extrusion rheometer (GER). The gas extrusion rheometer is described by M. Shida, R. N. Shroff and L. V. Cancio in *Polymer Engineering Science,* Vol. 17, No. 11, p. 770 (1977), and in "Rheometers for Molten Plastics" by John Dealy, published by Van Nostrand Reinhold Co. (1982) on pp. 97–99, both of which are incorporated by reference herein in their entirety. GER experiments are performed at a temperature of 190° C., at nitrogen pressures between 250 to 5500 psig using a 0.0754 mm diameter, 20:1 L/D die with an entrance angle of 180° C. For the substantially linear ethylene polymers described herein, the PI is the apparent viscosity (in kpoise) of a material measured by GER at an apparent shear stress of $2.15\times10^6$ dyne/cm$^2$. The substantially linear ethylene polymers for use in the invention includes ethylene interpolymers and have a PI in the range of 0.01 kpoise to 50 kpoise, preferably 15 kpoise or less. The substantially linear ethylene polymers used herein have a PI less than or equal to 70 percent of the PI of a linear ethylene polymer (either a Ziegler polymerized polymer or a linear uniformly branched polymer as described by Elston in U.S. Pat. No. 3,645,992) having an $I_2$, $M_w/M_n$ and density, each within ten percent of the substantially linear ethylene polymers.

The rheological behavior of substantially linear ethylene polymers can also be characterized by the Dow Rheology Index (DRI), which expresses a polymer's "normalized relaxation time as the result of long chain branching." (See, S. Lai and G. W. Knight *ANTEC '93 Proceedings,* INSITE™ Technology Polyolefins (SLEP)—New Rules in the Structure/Rheology Relationship of Ethylene α-Oefin Copolymers, New Orleans, La., May 1993, the disclosure of which is incorporated herein by reference). DRI values range from 0 for polymers which do not have any measurable long chain branching (e.g., Tafmer™ products available from Mitsui Petrochemical Industries and Exact™ products available from Exxon Chemical Company) to about 15 and are independent of melt index. In general, for low to medium pressure ethylene polymers (particularly at lower densities) DRI provides improved correlations to melt elasticity and high shear flowability relative to correlations of the same attempted with melt flow ratios. For the substantially linear ethylene polymers useful in this invention, DRI is preferably at least 0.1, and especially at least 0.5, and most especially at least 0.8. DRI can be calculated from the equation:

$$DRI=(3652879*\tau_o^{1.00649}/\eta_o-1)/10$$

where $\tau_o$ is the characteristic relaxation time of the material and $\eta_o$ is the zero shear viscosity of the material. Both $\tau_o$ and $\eta_o$ are the "best fit" values to the Cross equation, i.e., $$\eta/\eta_o=1/(1+(\lambda*\tau_o)^{1-n})$$

in which n is the power law index of the material, and $\eta$ and $\lambda$ are the measured viscosity and shear rate, respectively. Baseline determination of viscosity and shear rate data are obtained using a Rheometric Mechanical Spectrometer (RMS-800) under dynamic sweep mode from 0.1 to 100 radians/second at 160° C. and a Gas Extrusion Rheometer (GER) at extrusion pressures from 1,000 psi to 5,000 psi (6.89 to 34.5 MPa), which corresponds to shear stress from 0.086 to 0.43 MPa, using a 0.0754 mm diameter, 20:1 L/D die at 190° C. Specific material determinations can be performed from 140° C. to 190° C. as required to accommodate melt index variations.

The substantially linear ethylene polymers used in the invention are also characterized by a single DSC melting peak. The single melting peak is determined using a differential scanning calorimeter standardized with indium and deionized water. The method involves 3–7 mg sample sizes, a "first heat" to about 180° C. which is held for 4 minutes, a cool down at 10° C./min. to −30° C. which is held for 3 minutes, and heat up at 10° C./min. to 140° C. for the "second heat". The single melting peak is taken from the "second heat" heat flow vs. temperature curve. Total heat of fusion of the polymer is calculated from the area under the curve.

For polymers having a density of 0.875 g/cc to 0.910 g/cc, the single melting peak may show, depending on equipment sensitivity, a "shoulder" or a "hump" on the low melting side that constitutes less than 12 percent, typically, less than 9 percent, and more typically less than 6 percent of the total heat of fusion of the polymer. Such an artifact is observable for other homogeneously branched polymers such as Exact™ resins and is discerned on the basis of the slope of the single melting peak varying monotonically through the melting region of the artifact. Such an artifact occurs within 34° C., typically within 27° C., and more typically within 20° C. of the melting point of the single melting peak. The heat of fusion attributable to an artifact can separately be determined by specific integration of its associated area under the heat flow vs. temperature curve.

The homogeneous linear and substantially linear ethylene polymers are analyzed by gel permeation chromatography (GPC) on a Waters 150° C. high temperature chromatographic unit equipped with differential refractometer and three columns of mixed porosity. The columns are supplied by Polymer Laboratories and are commonly packed with pore sizes of $10^3$, $10^4$, $10^5$ and $10^6$. The solvent is 1,2,4-trichlorobenzene, from which 0.3 percent by weight solutions of the samples are prepared for injection. The flow rate is 1.0 ml/min, unit operating temperature is 140° C., and the injection size is 100 microliters.

The molecular weight determination with respect to the polymer backbone is deduced by using narrow molecular weight distribution polystyrene standards (from Polymer Laboratories) in conjunction with their elution volumes. The equivalent polyethylene molecular weights are determined by using appropriate Mark-Houwink coefficients for polyethylene and polystyrene (as described by Williams and Ward in *Journal of Polymer Science,* Polymer Letters, Vol. 6, p. 621, 1968) to derive the equation $M_{polyethylene} = a \cdot (M_{polystyrene})^b$.

In this equation, a=0.4316 and b=1.0. Weight average molecular weight, $M_w$, is calculated in the usual manner according to the formula $$M_w = \Sigma(w_i \times M_i)$$

where $w_i$ and $M_i$ are the weight fraction and molecular weight, respectively, of the $i^{th}$ fraction eluting from the GPC column.

The homogeneous linear and substantially linear ethylene polymers useful in the invention are characterized as having a narrow molecular weight distribution ($M_w/M_n$), i.e., an $M_w/M_n$ which is less than 2.5. For the linear and substantially linear ethylene/α-olefin polymers, the $M_w/M_n$ is preferably from 1.5 to 2.5, more preferably from 1.8 to 2.2.

The homogeneous linear or substantially linear ethylene polymer will be an interpolymer of ethylene with at least one ethylenically unsaturated monomer, conjugated or nonconjugated diene, polyene, etc. Preferred comonomers include the $C_3$–$C_{20}$ α-olefins, especially propene, isobutylene, 1-butene, 1-hexene, 4-methyl-1-pentene, and 1-octene.

The dienes suitable as comonomers, particularly in the making of ethylene/α-olefin/diene terpolymers, are typically non-conjugated dienes having from 6 to 15 carbon atoms. Representative examples of suitable non-conjugated dienes that may be used to prepare the terpolymers include:

(a) Straight chain acyclic dienes such as 1,4-hexadiene; 1,5-heptadiene; and 1,6-octadiene;

(b) Branched chain acyclic dienes such as 5-methyl-1,4-hexadiene; 3,7-dimethyl-1,6-octadiene; and 3,7-dimethyl-1,7-octadiene;

(c) Single ring alicyclic dienes such as 4-vinylcyclohexene; 1-allyl-4-isopropylidene cyclohexane; 3-allylcyclopentene; 4-allylcyclohexene; and 1-isopropenyl-4-butenylcyclohexene;

(d) Multi-ring alicyclic fused and bridged ring dienes such as dicyclopentadiene; alkenyl, alkylidene, cycloalkenyl, and cycloalkylidene norbornenes, such as 5-methylene-2-norbornene; 5-methylene-6-methyl-2-norbornene; 5-methylene-6,6-dimethyl-2-norbornene; 5-propenyl-2-norbornene; 5-(3-cyclopentenyl)-2-norbornene; 5-ethylidene-2-norbornene; 5-cyclohexylidene-2-norbornene; etc.

The preferred dienes are selected from the group consisting of 1,4-hexadiene; dicyclopentadiene; 5-ethylidene-2-norbornene; 5-methylene-2-norbornene; 7-methyl-1,6 octadiene; piperylene; 4-vinylcyclohexene; etc.

Preferably the thermoplastic composition comprises at least one metallocene polyolefin having a melt index of less than about 10 g/10 min. and a density ranging from about 0.850 g/cm³ to about 0.965 g/cm³. More preferably, the melt index is less than about 1 g/10 min. and the density is less than about 0.890 g/cm². This relatively high molecular weight component contributes to the overall strength of the coating. When such a high molecular weight polymer is employed, it will be preferred that the thermoplastic composition additionally comprise a viscosity-reducing agent, such as a tackifier or a wax. In this regard, in one particularly preferred embodiment, the coating will comprise a second polyolefin having a melt index greater than about 500 g/10 min., and a density ranging from about 0.850 g/cm³ to about 0.900 g/cm³, more preferably from about 0.850 g/cm³ to about 0.890 g/cm³. Blending a relatively high molecular weight metallocene polyolefin with a lower molecular weight polyolefin reduces the overall viscosity of the polymer system. For polymer rich compositions, those in which the total polymer concentration is in excess of 50 wt-%, ultra low molecular weight polymers must be employed as diluents for the high molecular weight component to insure the complex viscosity falls within the rheological window. Ultra-low molecular weight polyolefins are defined as those polyolefins which exhibit a Brookfield viscosity at 350° F. of less than about 8,200 cps. For the present invention, the ultra-low molecular weight polyolefins preferably have a Brookfield viscosity less than about 5,000 cps at 350° F., and more preferably less than about 1,000 cps having a density ranging from about 0.850 g/m³ to about 0.950 g/m³. As melt viscosity at 350° F. may be correlated to melt index ($I_2$) and to number average molecular weight, the ultra-low molecular weight polyolefins will further be characterized as having an $I_2$ greater than about 1000 g/10 min., preferably greater than about 1,500 and more preferably greater than about 6,000. Likewise, the ultra-low molecular weight polyolefins will further be characterized as having a number average molecular weight of less than about 11,000, preferably less than about 10,000, and more preferably less than about 6,000.

Ultra-low molecular weight olefin polymers are disclosed and claimed in the patent application entitled Ultra-Low Molecular Weight Polymers, filed on Jan. 22, 1996 in the names of M. L. Finlayson, C. C. Garrison, R. E. Guerra, M. J. Guest, B. W. S. Kolthammer, D. R. Parikh, and S. M. Ueligger, incorporated herein by reference.

Ultra-low molecular weight ethylene/α-olefin interpolymers are especially advantageous in the present application, as they lead to a low polymer and formulation viscosity but are characterized by a peak crystallization temperature which is greater than that of corresponding higher molecular weight materials of the same density. In hot melt adhesive type applications, the increase in peak crystallization temperature translates to decreased close times, as the materials begins to crystallize from the hot melt more rapidly.

Compounded hot melt adhesives are preferred due to the ability to independently tailor the visco-elastic properties, open time, tack, and various other properties. Hot melt adhesives commonly have melt flow indices required for such processing already at very low temperatures. Typical hot melts are fluid enough for such processing at temperatures ranging from about 60° C. to 110° C.

More preferably, the thermoplastic composition exhibits certain rheological characteristics such that a continuous coating, especially a body fluid impermeable coating can be produced at coating weights of less than about 30 g/m². In general, the rheological properties preferably fall within a rheological window wherein the complex viscosity at high shear rates (1,000 rad/sec) is less than about 500 poise and the complex viscosity at low shear rates (<1 rad/sec) is between about 100 and about 1,000 poise. In other words, preferable thermoplastic compositions exhibit Newtonian regions at low shear rates and shear thinning at higher shear rates. Thermoplastic compositions having wide windows of application are those in which the composition exhibits the appropriate rheological properties at a variety of application settings, particularly low temperatures. Narrow application windows are those in which the rheological parameters are only met under very specific conditions. Amorphous polyolefins based hot melt adhesives such as Lunatack® D-8370 (H. B. Fuller Company) tend to exhibit relatively flat Brookfield viscosity curves and relatively wide application windows whereas block copolymer based hot melt adhesives tend to exhibit particularly steep Brookfield viscosity profiles and very narrow application windows.

Data generated that supports this rheological window is depicted in Table I. The test procedures used to determine the rheological data are described in detail hereinafter. The applicants surmise that the high shear rate data relates to the processing conditions at the slot die exit. A composition with too high of a complex viscosity at 1,000 radians/sec would require excessive pump pressure to exit the coating device. A die with a shim gap larger than 3 mm could be used to process these materials but a higher coating weight may result.

The low shear rate data relates to the settling of the coating on the substrate during the time it is suspended above the substrate. If the low shear value is too high, the coating may not adhere adequately to the substrate and/or the thermoplastic composition builds up at the nozzle causing a streaked, discontinuous coating. If the low shear viscosity is too low, the coating may seep into the substrate, causing poor barrier properties.

Extensional viscosity, which was not measured, can also strongly influence the melt strength. Higher levels of branching or the addition of a small concentration of a high molecular weight material can strongly influence the melt strength. More preferred, are compositions that meet the target rheological parameters at low application temperatures of less than about 160° C., more preferably less than about 125° C., most preferably less than about 110° C.

Other rheological properties predict draw resonance tendencies. Draw resonance is a term describing a thickening and thinning of the thermoplastic coating in the machine direction, as well as an oscillation in the width of the coating. Draw resonance is typically caused by the draw ratio being too high or the melt temperature being too hot. The draw ratio is the die gap divided by the final coating thickness. By decreasing the die gap or by increasing the coating weight, the draw ratio can be reduced, thereby reducing the stress on the thermoplastic composition. Too hot of a melt temperature causes the polymer to degrade and cross-link. This cross-linking can occur unevenly across the web, resulting in thick-thin variances in the gauge of the coating. Since the preferred coating method employs markedly low coating temperatures, draw resonsance is more likely to be caused by too high of a draw ratio rather than too hot of a temperature. Since many of the thermoplastic compositions coated herein are relatively transparent, draw resonance can be visually detected in the pulsing or shaking of the molten film web. As the majority of thermoplastic ingredients fluoresce in the presence of ultraviolet light, draw resonance and other inconsistencies in the coating can easily be detected by draping the coated laminate over a tubular style fluorescent bulb.

The applicants have found that thermoplastic compositions comprising metallocene polyolefins characterized by having a tan delta of less than 50, preferably less than 30 at 120° C. and at 0.1 rad/sec exhibit the proper balance of visco-elastic properties such that draw resonance does not occur, even at line speeds as high as 225 m/min.

The applicants surmise that certain rheological properties predict the moisture permeability. Thermoplastic compositions comprising polymers having high crystallinity (density greater than about 0.90 g/cm$^2$) have a negative effect on the moisture permeability. During moisture permeability testing the coating is stretched to some extent by the force of the fluid column. Thermoplastic compositions comprising highly crystalline polymers can not elongate without fracturing. This is typically not a problem with extruded films comprising neat resins such as polyethylene and polypropylene.

Accordingly, many known hot melt adhesive compositions are well suited for use in the coating method of this invention. Hot melt adhesives typically comprise at least one thermoplastic polymer, at least one plasticizer and at least one tackifying resin. Preferably, such suitable hot melts comprise up to 40% by weight of thermoplastic polymer, up to 40% by weight of a plasticizer and up to 70% by weight of tackifying resin.

With respect to the thermoplastic polymer, atactic polyalphaolefins such as Vestoplast® 708 (Hüls) and synthetic rubbers such as S-EB-S block copolymers have been found to be especially suited, particularly those as used in hot melt adhesives such as Lunatack® D-3964 (H. B. Fuller). Further, however, other thermoplastic polymers are also suitable, such as ethylenic copolymers including ethylenevinyl acetate, ethylene-methyl acrylate copolymers and mixtures thereof or other synthetic rubbers as available in commerce under the tradenames Kraton®, Solprene®, and Stereon®.

Preferably, the thermoplastic composition comprises at least one metallocene polyolefin having a melt index of less than about 10 g/10 min. and a density ranging from about 0.850 g/cm$^3$ to about 0.900 g/cm$^3$. In the case of polyolefins and ethylenic copolymers, polymer concentrations as high as 100 wt-% may be suitable. It should be noted that compositions useful for traditional extrusion die coating will not be suitable uncompounded for the coating method described herein. Such commercially available neat resins such as polypropylene and polyethylene do not have a sufficiently low enough complex viscosity at temperatures less than 160° C. to be coated in His manner. Furthermore, a single unimodal polymer of sufficiently low enough complex viscosity is typically high in density, greater than about 0.90 g/cm$^2$, due to being highly crystalline in nature, such neat polymer do not possess the proper balance of visco-elastic properties to be fluid-impermeable coating at low coating weights.

Plasticizers and tackifying resins used in hot melt adhesives are known. Oils such as naphthenic oils are preferred plasticizers. As for tackifying resins, those resins already known for such purposes are generally suitable, especially hydrocarbon resins, ester resins and other such compatible resins. The components are mixed and processed in a known manner to prepare the hot melts which can be used according to this invention.

With suitable hot melts, such as those described in DE-A-41 21 716, it is also possible to make materials which are impermeable to liquid water, yet water vapor permeable rendering the coating "breathable".

In addition to commonly known hot melt adhesives, thermoplastic compositions comprising a water soluble, saline (body fluid) insoluble copolyester such as Eastman AQ 1350®, commercially available from Eastman, are also particularly useful for creating barrier films that are impervious to body fluid, yet readily water soluble. This feature is of particular interest for creating flushable and compostable disposable hygienic products. Furthermore, there may be applications wherein water permeability is desired. Accordingly, this coating method may also be suitable for coating water permeable, water soluble and/or biodegradable thermoplastic materials.

Hereinafter, the invention will be further depicted by the following non-limiting examples. The amounts of the ingredients in the examples are expressed as a percentage by weight of the composition.

EMBODIMENT EXAMPLE 1

Several hot melts which slightly differ from each other in composition were formulated in the following composition ranges:

20–25% naphthenic oil
30–40% atactic polyolefin(s)
35–45% hydrocarbon resin

EMBODIMENT EXAMPLE 2

Several hot melts were formulated within the following range limits:

15–20% SIS-block copolymer
15–25% naphthenic oil
50–65% ester resin

EMBODIMENT EXAMPLE 3

As a commercially available hot melt adhesive, the "Lunatack D 8370" product was used, which is available from H. B. Fuller GmbH. This is a hot-melt adhesive comprising about 35% polyolefin, about 40% hydrocarbon resin with a cyclopentadiene component, about 15% polyisobutylene and about 10% naphthenic oil.

EMBODIMENT EXAMPLES 4–16

Table 1 depicts rheological data for examples 4 through 16. Column 2 of Table 1 depicts the reference temperature for the rheological parameters as well as the coating application temperature utilized for each sample. Table 2 depicts the chemical description of examples 4 through 9 as well as the coating parameters for those examples in which a continuous coating resulted. A consistent continuous coating was not able to be produced with examples 4 through 9 at the temperature indicated in Column 2. The applicants surmise that the inability to produce a continuous coating is due to the complex viscosity being greater than about 1000 poise at about 1 rad/sec. Although examples 4 and 5 could not produce a continuous coating at low application temperatures, by increasing the temperature the complex viscosity at 1 rad/sec could be forced into the rheological window as is demonstrated by examples 10 and 14. By comparing example 7 with 16, the applicants have demonstrated the relatively narrow rheological window of Lunatack® D-3964. At 90° C., D-3964 exhibits too high of a complex viscosity at 1 rad/sec. At 110° C., D-3964 exhibits too low of a complex viscosity at 1 rad/sec to produce a continuous coating at low coating weights, causing the material to soak into the substrate. The applicants surmise a temperature exists between 90° C. and 110° C. wherein D-3964 would produce a continuous coating. However, a thermoplastic composition exhibiting such a narrow rheological window would have little chance of commercial success. Example 14 exhibits the utility of blending a thermoplastic composition that does not meet the rheological window with another material such that the resulting composition is useful for producing a continuous coating. In this particular example, since D-3964 exhibits too low of a complex viscosity at 1 rad/sec to produce a continuous coating at a coat weight of about 10 g/m$^2$, it is blended with a material to raise the complex viscosity at 1 rad/sec to improve the shear thinning properties such that the blend exhibits the preferable rheological properties. Alternatively, examples exhibiting too high of a complex viscosity at 1 rad/sec, such as examples 4 through 9 can be blended with compatible materials to lower the complex viscosity such that the blended material may be coated at the preferable application temperature of less than 165° C.

EMBODIMENTS 18–45

Catalyst Preparation

Part 1: Preparation of TiCl$_3$(DME)$_{1.5}$

The apparatus (referred to as R-1) was set-up in the hood and purged with nitrogen; it consisted of a 10 L glass kettle with flush mounted bottom valve, 5-neck head, polytetrafluoroethylene gasket, clamp, and stirrer components (bearing, shaft, and paddle). The necks were equipped as follows: stirrer components were put on the center neck, and the outer necks had a reflux condenser topped with gas inlet/outlet, an inlet for solvent, a thermocouple, and a stopper. Dry, deoxygenated dimethoxyethane (DME) was added to the flask (approx. 5.2 L). In the drybox, 300 g of TiCl$_3$ was weighed into an equalizing powder addition funnel; the funnel was capped, removed from the drybox, and put on the reaction kettle in place of the stopper. The TiCl$_3$ was added over about 10 minutes with stirring. After the addition was completed, additional DME was used to wash the rest of the TiCl$_3$ into the flask. This process was then repeated with 325 g of additional TiCl$_3$, giving a total of 625 g. The addition funnel was replaced with a stopper, and the mixture heated to reflux. The color changed from purple to pale blue. The mixture was heated for about 5 hours, cooled to room temperature, the solid was allowed to settle, and the supernatant was decanted from the solid. The TiCl$_3$(DME)$_{1.5}$ was left in R-1 as a pale blue solid.

Part 2: Preparation of [(Me$_4$C$_5$)SiMe$_2$N-t-Bu][MgCl]$_2$

The apparatus (referred to as R-2) was set-up as described for R-1, except that flask size was 30 L. The head was equipped with seven necks; stirrer in the center neck, and the outer necks containing condenser topped with nitrogen inlet/outlet, vacuum adapter, reagent addition tube, thermocouple, and stoppers. The flask was loaded with 7 L of toluene, 3.09 kg of 2.17 M i-PrMgCl in Et$_2$O, 250 mL of THF, and 1.03 kg of (Me$_4$C$_5$H)SiMe$_2$NH-t-Bu. The mixture was then heated, and the ether allowed to boil off into a trap cooled to −78° C. After three hours, the temperature of the mixture had reached 80° C., at which time a white precipitate formed. The temperature was then increased to 90° C. over 30 minutes and held at this temperature for 2 hours. At the end of this time, the heater was turned off, and 2 L of DME was added to the hot, stirring solution, resulting in the formation of additional precipitate. The solution was allowed to cool to room temperature, the material was allowed to settle, and the supernatant was decanted from the solid. An additional wash was done by adding toluene, stirring for several minutes, allowing the solids to settle, and decanting the toluene solution. The [(Me$_4$C$_5$)SiMe$_2$N-t-Bu][MgCl]$_2$ was left in R-2 as an off-white solid.

Part 3: Preparation of [($\eta$5-Me$_4$C$_5$)SiMe$_2$N-t-Bu]Ti($\eta^4$-1,3-pentadiene)

The materials in R-1 and R-2 were slurried in DME (the total volumes of the mixtures were approx. 5 L in R-1 and 12 L in R-2). The contents of R-1 were transferred to R-2 using a transfer tube connected to the bottom valve of the 10 L flask and one of the head openings in the 30 L flask. The remaining material in R-1 was washed over using additional DME. The mixture darkened quickly to a deep red/brown color. After 15 minutes, 1050 mL of 1,3-pentadiene and 2.60 kg of 2.03 M n-BuMgCl in THF were added simultaneously. The maximum temperature reached in the flask during this addition was 53° C. The mixture was stirred for 2 hours, then approx. 11 L of solvent was removed under vacuum. Hexane was then added to the flask to a total volume of 22 L. The material was allowed to settle, and the liquid layer (12 L) was decanted into another 30 L glass kettle (R-3). An additional 15 liters of product solution was collected by adding hexane to R-2, stirring for 50 minutes, again allowing to settle, and decanting. This material was combined with the first extract in R-3. The solvent in R-3 was removed under vacuum to leave a red/black solid, which was then extracted with toluene. This material was transferred into a storage cylinder. Analysis indicated that the solution (11.75 L) was 0.255 M in titanium; this is equal to 3.0 moles of [($\eta$5-$Me_4C_5$)$SiMe_2$N-t-Bu]Ti($\eta$4-1,3-pentadiene) or 1095 g. This is a 74% yield based on the titanium added as $TiCl_3$.

Polymer Descriptions

The polymers employed in the embodiments 18–45 comprise at least one substantially linear ethylene/1-octene interpolymer. The properties of the polymers are set forth in the following Table A:

The ethylene and the hydrogen, as well as any ethylene and hydrogen which were recycled from the separator, were combined into one stream before being introduced into the diluent mixture, a mixture of $C_8$–$C_{10}$ saturated hydrocarbons, e.g., ISOPAR™-E (available from Exxon Chemical Company) and the comonomer 1-octene.

The metal complex and cocatalysts were combined into a single stream and were also continuously injected into the reactor. The catalyst was as prepared in the catalyst description set forth above; the primary cocatalyst was tri (pentafluorophenyl)borane, available from Boulder Scientific as a 3 wt-% solution in ISOPAR-E mixed hydrocarbon; and the secondary cocatalyst was modified methylalumoxane (MMAO Type 3A), available from Akzo Nobel Chemical Inc. as a solution in heptane having 2 wt-% aluminum.

Sufficient residence time was allowed for the metal complex and cocatalyst to react prior to introduction into the polymerization reactor. The reactor pressure was held constant at about 475 psig.

After polymerization, the reactor exit stream was introduced into a separator where the molten polymer was separated from the unreacted comonomer(s), unreacted ethylene, unreacted hydrogen, and diluent mixture stream, which was in turn recycled for combination with fresh comonomer, ethylene, hydrogen, and diluent, for introduction into the reactor. The molten polymer was subsequently strand chopped or pelletized, and, after being cooled in a water bath or pelletizer, the solid pellets were collected. Table B describes the polymerization conditions and the resultant polymer properties.

TABLE A

|  | Density (g/cc) | Melt Index ($I_2$) (g/10 min.) | Melt Viscosity at 350° C. | $I_{10}/I_2$ | Deionized water (ppm) | Calcium Stearate (ppm) | Irganox 1076 (Polymers A–F) Irganox 1010 (Polymers G–J) (ppm) | PEPQ (ppm) | Eru (ppm) |
|---|---|---|---|---|---|---|---|---|---|
| Polymer A | 0.890 |  | 5000 |  | 0 |  | 2000 | 0 | 0 |
| Polymer B | 0.902 | 30 |  | 7.0 | 0 | 1250 | 500 | 800 | 600 |
| Polymer C | 0.870 | 30 |  |  | 0 | 1250 | 500 | 800 | 600 |
| Polymer D Dual MI | 30% 0.868 70% 0.868 | 0.5 1000 |  | 11.5 | 0 | 1250 | 500 | 800 | 600 |
| Polymer E | 0.870 | 5 |  |  | 0 | 1250 | 500 | 800 | 0 |
| Polymer F | 0.863 | 0.5 |  |  | 0 | 1250 | 500 | 800 | 0 |
| Polymer G Dual MI | 30% 0.875 70% 0.875 | 0.1 1400 |  |  | 35 | 0 | 2000 | 0 | 0 |
| Polymer H Dual MI/Density | 30% 0.880 70% 0.858 | 0.1 5000 mPa |  |  | 35 | 0 | 2000 | 0 | 0 |
| Polymer I | 0.858 | 30 |  |  | 35 | 0 | 2000 | 0 | 0 |
| Polymer J | 0.881 | 2200 | 5000 |  | 35 | 0 | 2000 | 0 | 0 |

PEPQ refers to tetrakis-(2,4-di-tert-butyl-phenyl)-4,4' biphenylphosphonite, available from Clariant Chemical. Irganox 1076 and 1010 are hindered phenolic antioxidants available from Ciba-Geigy Corporation. Eru refers to erucamide fatty acid slip agent, available from Croda (United Kingdon) and Witco Chemical Company.

Polymers B, C, E, F, and I are prepared in accordance with the procedures set forth in U.S. Pat. Nos. 5,272,236 and 5,278,272 incorporated herein by reference.

Preparation of Ultra-Low Molecular Weight Ethylene Polymers:

Polymers A and J are prepared in a solution polymerization process using a well-mixed recirculating loop reactor. Each polymer was stabilized with 35 ppm deionized water (as a catalyst kill agent).

TABLE B

|  | A | J(C10R6) |
|---|---|---|
| Ethylene fresh feed rate (lbs/hr) | 140 | 105 |
| Total ethylene feed rate (lbs/hr) | 146.17 | 110.4 |
| Fresh octene feed rate (lbs/hr) | 49.5 | 50 |
| Total octene feed rate (lbs/hr) | 112 | 100.6 |
| Total octene concentration (weight %) | 11.4 | 13.7 |
| Fresh hydrogen feed rate (standard $cm^3$/min) | 5350 | 3500 |
| Solvent and octene feed rate (lbs/hr) | 839.4 | 629.4 |
| Ethylene conversion rate (wt %) | 90.3 | 90.7 |
| Reactor temperature (° C.) | 119.8 | 120 |
| Feed temperature (° C.) | 15 | 15 |

TABLE B-continued

|  | A | J(C10R6) |
|---|---|---|
| Catalyst concentration (ppm) | 70 | 20 |
| Catalyst flow rate (lbs/hr) | 1.265 | 4.125 |
| Primary cocatalyst concentration (ppm) | 2031 | 1500 |
| Primary cocatalyst flow rate (lbs/hr) | 1.635 | 1.760 |
| Primary cocatalyst to catalyst molar ratio (B:Ti) | 3.48 | 2.971 |
| Secondary cocatalyst concentration (ppm) | 198 | 125 |
| Secondary cocatalyst flow rate (lbs/hr) | 1.258 | 1.868 |
| Secondary cocatalyst to catalyst molar ratio (Al:Ti) | 4.986 | 4.975 |
| Product density (g/cm$^3$) | 0.8925 | 0.880 |
| Product melt viscosity at 350° F. (centipoise) | 4,000 | 5000 |
| Polymer melt index (I$_2$ at 190° C.)* | 1,900* | |
| Polymer Mn | 8,900* | |

*Calculated on the basis of melt viscosity correlations in accordance with the formulas:
$I_2 = 3.6126(10^{\log(h)-6.6928})^{-1.1363}-9.3185$,
$Mn = 10^{[(\log h + 10.46)/3.56)]}$
where h = melt viscosity at 350° F.

Preparation of Dual Reactor Produced Polymers

Polymers D, F and G are prepared in accordance with the following procedure:

The ethylene and the hydrogen, as well as any ethylene and hydrogen which were recycled from the separator, were combined into one stream before being introduced into the diluent mixture, a mixture of C$_8$–C$_{10}$ saturated hydrocarbons, e.g., ISOPAR™-E (available from Exxon Chemical Company) and the comonomer 1-octene.

The metal complex and cocatalysts were combined into a single stream and were also continuously injected into the first polymerization reactor. The catalyst was as prepared in the catalyst description set forth above; the primary cocatalyst was tri(pentafluorophenyl)borane, available from Boulder Scientific as a 3 wt-% solution in ISOPAR-E mixed hydrocarbon; and the secondary cocatalyst was modified methylalumoxane (MMAO Type 3A), available from Akzo Nobel Chemical Inc. as a solution in heptane having 2 wt-% aluminum.

Sufficient residence time was allowed for the metal complex and cocatalyst to react prior to introduction into the first polymerization reactor. The reactor pressure was held constant at about 475 psig. The reaction product of the first polymerization reactor is transferred to a second reactor, which is operated in series with the first reactor. The ethylene concentration in the exit stream from the first polymerization reactor is less than four percent, indicating the presence of long chain branching as described in U.S. Pat. No. 5,272,236.

As in the case of the first polymerization reactor, the ethylene and the hydrogen, as well as any ethylene and hydrogen which were recycled from the separator, were combined into one stream before being introduced into the diluent mixture, a mixture of C$_8$–C$_{10}$ saturated hydrocarbons, e.g., ISOPAR™-E (available from Exxon Chemical Company) and the comonomer 1-octene. The metal complex and cocatalysts were the same as those used in the first polymerization reactor, and were combined into a single stream and were also continuously injected into the second polymerization reactor. The reactor pressure was held constant at about 475 psig.

After polymerization in the second polymerization reactor, the resultant polymer composition was transferred to a separator where the molten polymer was separated from the unreacted comonomer(s), unreacted ethylene, unreacted hydrogen, and diluent mixture stream, which was in turn recycled for combination with fresh comonomer, ethylene, hydrogen, and diluent, for introduction into the first polymerization reactor. The molten polymer was subsequently strand chopped or pelletized, and, after being cooled in a water bath or pelletizer, the solid pellets were collected. Table C describes the polymerization conditions and the resultant polymer properties.

TABLE C

|  | Polymer F (C10R1) | Polymer G (C10R2) |
|---|---|---|
| First reactor fresh ethylene feed rate (kg/hr) | 65 | 65 |
| First reactor total ethylene feed rate (kg/hr) | 68 | 68 |
| First reactor fresh octene feed rate (kg/hr) | 31 | 44 |
| First reactor total octene feed rate (kg/hr) | 78.5 | 89 |
| First reactor octene concentration (wt. %) | 16.1 | 18.3 |
| First reactor diluent and octene feed rate (kg/hr) | 422 | 422 |
| Fresh hydrogen feed rate (standard cm$^3$/min) | 50.25 | 20.75 |
| First reactor catalyst concentration (ppm Ti) | 3.96 | 3.96 |
| First reactor catalyst flow rate (kg/hr) | 1.525 | 1.659 |
| First reactor primary cocatalyst concentration (ppm B) | 215 | 215 |
| First reactor primary cocatalyst flow rate (kg/hr) | 0.879 | 0.957 |
| First reactor secondary cocatalyst concentration (ppm Al) | 22 | 22 |
| First reactor secondary cocatalyst flow rate (kg/hr) | 0.751 | 0.840 |
| First reactor molar ratio of Ti:B:Al | 1:3:5 | 1:3:5 |
| First reactor feed temperature (° C.) | 15 | 15 |
| First reactor temperature (° C.) | 80 | 80 |
| First reactor ethylene conversion rate (wt. %) | 64 | 63 |
| First reactor product targeted density (g/cm$^3$) | 0.875 | 0.870 |
| First reactor product targeted melt index (12) (g/10 min.) | 0.4 | 0.4 |
| Second reactor fresh ethylene feed rate (kg/hr) | 85 | 85 |
| Second reactor total ethylene feed rate (kg/hr) | 86.8 | 86.8 |
| Second reactor fresh octene feed rate (kg/hr) | 56 | 33 |
| Second reactor total octene feed rate (kg/hr) | 80.2 | 59.5 |
| Second reactor octene concentration (wt. %) | 23.6 | 17.5 |
| Second reactor diluent and octene feed rate (kg/hr) | 255 | 255 |
| Fresh hydrogen feed rate (standard cm$^3$/min) | 9500 | 11,265 |
| Second reactor catalyst concentration (ppm Ti) | 105 | 105 |
| Second reactor catalyst flow rate (kg/hr) | 2.947 | 3.816 |
| Second reactor primary cocatalyst concentration (ppm B) | 2499 | 2499 |
| Second reactor primary cocatalyst flow rate (kg/hr) | 3.968 | 5.141 |
| Second reactor secondary cocatalyst concentration (ppm Al) | 249 | 249 |
| Second reactor secondary cocatalyst flow rate (kg/hr) | 3.50 | 4.534 |
| Second reactor molar ratio of Ti:B:Al | 1:3:5 | 1:3:5 |
| Second reactor feed temperature (° C.) | 15 | 15 |
| Second reactor temperature (° C.) | 135 | 135 |
| Second reactor ethylene conversion rate (wt. %) | 55 | 89.3 |
| Second reactor product targeted density (g/cm3) | 0.875 | 0.890 |
| Second reactor product targeted melt index (12) (g/10 min.) | 465 | 465 |

Polymer D is prepared by a process such as described in the polymerization of Polymers F and G, with the polymerization conditions being adjusted to yield approximately 30 wt-% of a first reactor product having a density of 0.860 g/cm$^3$ and an I$_2$ of 0.09 g/10 min. and approximately 70 wt-% of a second reactor product having a density of 0.868 g/cm$^3$ and an I$_2$ of 274 g/10 min.

Test Methods

Coating Procedure

The hot melts according to embodiment examples 1 through 3 were placed in a customary processing machine provided with a slot nozzle such as Nordson EP 51. The slot nozzle was provided horizontally facing a roller over which a 23 g/m$^2$ basis weight spunbond polypropylene nonwoven (Corovin® A23A40 Corosoft-Plus, Corovin GmbH) was led in an upward direction. The distance between the slot nozzle and the substrate was 2 mm, at a nozzle slot length of 70 mm. The web speed of the nonwoven was 25 m/min. At a system pressure of about 53 bar and a release temperature of the hot melt of approximately 100° C., the hot melt was coated onto the substrate, where it formed a closed barrier layer. Immediately thereafter, the thus coated substrate was adhered to a customary absorptive body (tissue). In each case, a reliable adhesive bond between substrate and tissue was provided, and in each case, the hot melt barrier layer formed between the tissue and the substrate was found to be completely liquid-impermeable. Processing was without any problems. The coating weight was an average of 21 g/m². At corresponding fine adjustment of release temperature of hot melt, system pressure, distance between slot nozzle and substrate, machine speed etc. etc., it was systematically possible to form water-tight closed barrier layers at area weights of less than 20 g/m² on this substrate.

Examples 4 through 45 were coated in a similar manner as examples 1–3 with the exception that the continuous coating was not adhered to tissue. The application conditions and rheological data of the adhesive compositions are depicted in Table 1. A system pressure ranging from about 40 to about 65 bar was obtained during coating of examples 10 through 16.

Examples 18–19 comprise at least one substantially linear interpolymer of ethylene. The compositions are depicted in Table 3 A,B,C, & D. The application conditions and water permeability resistance are depicted in Table 4 A & B.

Rheological Testing

The rheological data was generated from a dynamic mechanical spectrometer such as a Rheometric Scientific RDS 7700 (10,000 g/cm transducer, 10 g/cm—<10,000 g/cm torque). A master curve of G' (shear storage modulus), G" (shear loss modulus) and complex viscosity as a function of frequency was obtained through time temperature superposition. During testing the sample was loaded at the upper test temperature between 50 mm diameter parallel plate discs with a 1 to 2 mm gap. After allowing the sample temperature to stabilize for at least about 10 minutes, a frequency sweep was performed from about 0.1 to about 100 radians per second. Upon the completion of the frequency sweep, the sample temperature was lowered to the next temperature and the procedure repeated. The strain amplitude was adjusted to improve the resolution and ranged from about 20% to about 40%. After the frequency sweep was completed at the final, lowest temperature, time-temperature superposition was used to overlay the data into a single master curve at the application temperature. If the actual coating temperature was not one of the actual temperatures tested, the Williams, Landel, Ferry (WLF) (Ferry, J. D. *Viscoelastic Properties of Polymers,* 3rd Ed., Wiley: NY, 1980) equation was used to obtain the master curve.

Time-temperature superposition can be applied for amorphous compositions as well as for crystalline compositions above the melt point. Capillary rheometry could be used to measure viscosity at high shear rates.

Melt Index

The melt index is measured in accordance with ASTM D-1238, condition 190° C./2.16 kg.

Density

The density is measured in accordance with ASTM D-792. The samples were annealed at ambient conditions for 24 hours before the measurement was taken.

Melt viscosity is determined in accordance with the following procedure using a Brookfield Laboratories DVII+ Viscometer in disposable aluminum sample chambers. The spindle used is a SC-31 hot-melt spindle, suitable for measuring viscosities in the range of from 10 to 100,000 centipoise. A cutting blade is employed to cut samples into pieces small enough to fit into the 1 inch wide, 5 inches long sample chamber. The sample is placed in the chamber, which is in turn inserted into a Brookfield Thermosel and locked into place with bent needle-nose pliers. The sample chamber has a notch on the bottom that fits the bottom of the Brookfield Thermosel to ensure that the chamber is not allowed to turn when the spindle is inserted and spinning. The sample is heated to 350° F., with additional sample being added until the melted sample is about 1 inch below the top of the sample chamber. The viscometer apparatus is lowered and the spindle submerged into the sample chamber. Lowering is continued until brackets on the viscometer align on the Thermosel. The viscometer is turned on, and set to a shear rate which leads to a torque reading in the range of 30 to 60 percent. Readings are taken every minute for about 15 minutes, or until the values stabilize, at which time the final reading is recorded.

Water permeability

The coated nonwoven was tested according to EDANA 160.0-89 "Wet Barrier" test method. The samples were conditioned for 24 hours at 50%+/−2% relative humidity, 23° C.+/−2° C. prior to testing. The samples were fixed (hot melt surface facing the water) to a cylindrical vessel, fitted with a bolted ring for clamping samples with a circular test area. The water pressure was increased recording the values the first drop (rather than the third as described in ERT 120.1-80) appeared on the surface of the nonwoven.

TABLE I

| Example | Temp. (° C.) | Complex Viscosity 1 rad/sec (poise) | Complex Viscosity $10^3$ rad/sec (poise) | G' 1 rad/sec (dynes/cm²) | Crossover Frequency (rad/sec) | Tan delta @ 1 rad/sec | Slope = Visc @ 1/1000 rad/sec | Continuous Coating Formed yes/no |
|---|---|---|---|---|---|---|---|---|
| 4 | 125 | 15000 | 100 | 10000 | 1 | 1 | 150 | no |
| 5 | 90 | 10000 | 300 | 3000 | 300 | 3 | 33 | no |
| 6 | 120 | 4500 | 1500 | 300 | 1000 | 30 | 4.5 | no |
| 7 | 90 | 3000 | 100 | 400 | 50 | 7 | 30 | not tested |
| 8 | 110 | 2000 | 500 | 700 | 10000 | 3 | 4 | no |
| 9 | 140 | 1000 | 500 | 50 | >1000 | 70 | 2 | no |
| 10 | 160 | 200 | 200 | 5 | >1000 | 4 | 1.25 | yes |
| 11 | 125 | 800 | 100 | 5000 | 20 | 1 | 8 | yes |
| 12 | 125 | 800 | 100 | 100 | 1000 | 10 | 8 | yes |
| 13 | 125 | 300 | 50 | 200 | 1 | 1 | 6 | not tested |
| 14 | 110 | 300 | 50 | 20 | 7000 | 20 | 6 | yes |
| 15 | 128 | 100 | 80 | 10 | 1000 | 10 | 1.25 | yes |
| 16 | 110 | 100 | 3.5 | 8 | 100 | 25 | 28 | no |

TABLE II

| Example | Tradename(s) | Chemical Description | Coating Weight(GSM) | Speed M/MIN | Permeability cm³ of H₂O pressure |
|---|---|---|---|---|---|
| 4 | 347-BD-19 (H. B. Fuller) | atactic polyolefin hot melt adhesive (HMA) | | | |
| 5 | D-3964 + 10% Vestoplast ® 750 | SEBS block copolymer/hydrocarbon resin/napthenic oil HMA + atactic polyolefin | | | |
| 6 | Eastman AQ ® 1350 | water dispersible copolyester (WO 95/18191) | | | |
| 7 | D-3964 | SEBS block copolymer/hydrocarbon resin/napthenic oil HMA | | | |
| 8 | NP-2085 (HBF) | urethane | | | |
| 9 | Eastman AQ ® 1350 | See Example 6 | | | |
| 10 | Eastman AQ ® 1350 | See Example 6 | | | |
| 11 | Vestoplast ® 703 (Huls) | atactic polyolefin | 22 | 30 | — |
| 12 | 347-BD-33 (HBF) | atactic polyolefin HMA | 10 | 30 | 100 |
| 13 | Vestoplast ® 703 + 10% Paraflint H4 | atactic polyolefin + Fischer Tropsch wax | | | |
| 14 | D-3964 + 10% Vestoplast 750 | SEBS block copolymer/hydrocarbon resin/napthenic oil HMA + atactic polyolefin | 9–11 | 34 | 50 |
| 15 | D-8370 | atactic polyolefin HMA | 12 | 30 | 46 |
| 16 | D-3964 | See Example 7 | 8 | 30 | — |
| 17 | Vestoplast ® 750 + 10% Wax | See Example 13 | 15–16 | 30 | — |

TABLE III A

| Tradename (Supplier) | Description | 18 | 19 |
|---|---|---|---|
| Polymer A (Dow) | Substantially linear interpolymer (SLEP) | | |
| Polymer B (Dow) | Substantially linear interpolymer | | |
| Polymer C (Dow) | Substantially linear interpolymer | | |
| Polymer D (Dow) | Dual melt index substantially linear interpolymer | 25.00 | 35.00 |
| Polymer E (Dow) | Substantially linear interpolymer | | |
| Polymer F (Dow) | Substantially linear interpolymer | | |
| Polymer G (Dow) | Dual melt index substantially linear interpolymer | | |
| Polymer H (Dow) | Dual melt index/dual density SLEP | | |
| Polymer I (Dow) | Substantially linear interpolymer | | |
| Polymer J (Dow) | Substantially linear interpolymer | | |
| Catenex 4142 (Shell) | mineral oil | 25.00 | |
| Petrobras K 521 (A. Kochen Gmb) | microwax TP 80 C | | 17.50 |
| Shell HMP (D. Shell AG) | microwax TP 90–100 C | | |
| Vestowax H2 TP 100C (Huls) | Fischer - Tropsch wax TP approx. 100 C | | |
| Sasol H4 (A. Kochen GmbH) | Fischer - Tropsch wax TP approx. 100 C | | |
| Eastotac R100H (Eastman) | hydrocarbon resin MP approx. 100 C | 50.00 | 47.50 |
| Eastotac H 130 (Eastman) | hydrocarbon resin MP approx. 130 C | | |
| Wingtack 95 (Weber & Schaer) | hydrocarbon resin | | |
| Lacqtene 1200MN 18C (Elf AtoChem) | Linear low density polyethylene (LLDPE), 20 melt index | | |
| PT 7007 (Dow) | LLDPE MI 7.5 | | |
| LD780R (DOW) | LLDPE | | |
| LE Wachs 114 (Leuna-Werke GmbH) | wax | | |
| TIO2 - preblend PE based (H. B. Fuller) | TIO2 - pre blend PE based | | |
| TIO2 - preblend EVA based (H. B. Fuller) | TIO2 - pre blend EVA based | | |
| Irganox 1010 FF (Ciba Additive GmbH) | antioxidant stabilizer | | |
| Irganox PS800 (Ciba Additive GmbH) | antioxidant stabilizer | | |

TABLE III B

| Tradename (Supplier) | 20 | 21 | 22 | 23 | 24 | 25 | 26 | 27 | 28 |
|---|---|---|---|---|---|---|---|---|---|
| Polymer A (Dow) | | 27.50 | | | | | | | |
| Polymer B (Dow) | | | | | | | | | |
| Polymer C (Dow) | | 27.50 | 30.00 | | | | | | |
| Polymer D (Dow) | | | | 25.00 | | 30.00 | 25.00 | 30.00 | 30.00 |
| Polymer E (Dow) | 25.00 | | | | 20.00 | | | | |
| Polymer F (Dow) | | | | | | | | | |
| Polymer G (Dow) | | | | | | | | | |
| Polymer H (Dow) | | | | | | | | | |
| Polymer I (Dow) | | | | | | | | | |
| Polymer J (Dow) | | | | | | | | | |
| Catenex 4142 (Shell) | 25.00 | | | | 25.00 | | | 5.00 | 10.00 |
| Petrobras K 521 (A. Kochen Gmb) | | 20.00 | 17.50 | 17.50 | | | 17.50 | | |
| Shell HMP (D. Shell AG) | | | | | | | | | |
| Vestowax H2 TP 100C (Huls) | | | | | | 20.00 | | 20.00 | |

TABLE III B-continued

| Tradename (Supplier) | 20 | 21 | 22 | 23 | 24 | 25 | 26 | 27 | 28 |
|---|---|---|---|---|---|---|---|---|---|
| Sasol H4 (A. Kochen GmbH) | | | | | | | | | 20.00 |
| Eastotac R100H (Eastman) | 50.00 | 20.00 | 47.50 | 47.50 | 50.00 | 50.00 | 47.50 | 45.00 | 40.00 |
| Eastotac H130 (Eastman) | | | | | | | | | |
| Wingtack 95 (Weber & Schaer) | | | | | | | | | |
| Lacqtene 1200MN18C (Elf AtoChem) | 5.00 | 5.00 | 5.00 | | 10.00 | | 10.00 | | |
| PT 7007 (Dow) | | | | 10.00 | | | | | |
| LD780R (DOW) | | | | | | | | | |
| LE Wachs 114 (Leuna-Werke GmbH) | | | | | | | | | |
| TIO2 preblend PE based (H. B. Fuller) | | | | | | | | | |
| TIO2 - preblend EVA based (H. B. Fuller) | | | | | | | | | |
| Irganox 1010 FF (Ciba Additive GmbH) | | | | | | | | | |
| Irganox PS800 (Ciba Additive GmbH) | | | | | | | | | |

TABLE III C

| Tradename (Supplier) | 29 | 30 | 31 | 32 | 33 | 34 | 35 | 36 | 37 |
|---|---|---|---|---|---|---|---|---|---|
| Polymer A (Dow) | | | | | | | | | |
| Polymer B (Dow) | | | | | | | | | |
| Polymer C (Dow) | | | | | | | | | |
| Polymer D (Dow) | | 30.00 | 30.00 | 30.00 | 30.00 | 30.00 | 30.00 | | |
| Polymer E (Dow) | | | | | | | | | |
| Polymer F (Dow) | | | | | | | | | |
| Polymer G (Dow) | | | | | | | | 30.00 | 35.00 |
| Polymer H (Dow) | | | | | | | | 30.00 | |
| Polymer I (Dow) | | | | | | | | | |
| Polymer J (Dow) | | | | | | | | | |
| Catenex 4142 (Shell) | 10.00 | | | | | | | | |
| Petrobras K 521 (A. Kochen Gmb) | | 7.50 | | | | 7.50 | 7.50 | 7.50 | 6.60 |
| Shell HMP (D. Shell AG) | | | | | 20.00 | | | | |
| Vestowax H2 TP 100C (Huls) | | | | | | | | | |
| Sasol H4 (A. Kochen GmbH) | 20.00 | 12.50 | 20.00 | | | 12.50 | 12.50 | 12.50 | 10.90 |
| Eastotac R100H (Eastman) | 40.00 | 49.70 | 29.70 | 44.70 | 49.70 | | 49.70 | 49.70 | 47.20 |
| Eastotac H130 (Eastman) | | | | | | | | | |
| Wingtack 95 (Weber & Schaer) | | | | | | 49.70 | | | |
| Lacqtene 1200MN18C (Elf AtoChem) | | | | | | | | | |
| PT 7007 (Dow) | | | | | | | | | |
| LD780R (DOW) | | | | | | | | | |
| LE Wachs 114 (Leuna-Werke GmbH) | | | | 20.00 | | | | | |
| TIO2 - preblend PE based (H. B. Fuller) | 20.00 | | 20.00 | | | | | | |
| TIO2 - preblend EVA based (H. B. Fuller) | | | | 5.00 | | | | | |
| Irganox 1010 FF (Ciba Additive GmbH) | | 0.15 | 0.15 | 0.15 | 0.15 | 0.15 | 0.15 | 0.15 | 0.15 |
| Irganox PS800 (Ciba Additive GmbH) | | 0.15 | 0.15 | 0.15 | 0.15 | 0.15 | 0.15 | 0.15 | 0.15 |

TABLE III D

| Tradename (Supplier) | 38 | 39 | 40 | 41 | 42 | 43 | 44 | 45 |
|---|---|---|---|---|---|---|---|---|
| Polymer A (Dow) | | | | | | | | |
| Polymer B (Dow) | | | | | | 8.00 | | |
| Polymer C (Dow) | | | 5.00 | | | | | |
| Polymer D (Dow) | | | | | | | 10.00 | 10.00 |
| Polymer E (Dow) | | | | | 8.00 | | | |
| Polymer F (Dow) | | | | | | | | |
| Polymer G (Dow) | 40.00 | 30.00 | 30.00 | | 30.00 | 30.00 | | |
| Polymer H (Dow) | | | | 30.00 | | | 10.00 | 20.00 |
| Polymer I (Dow) | | | | 4.00 | | | | |
| Polymer J (Dow) | | | | | | | 20.00 | 20.00 |
| Catenex 4142 (Shell) | | | | | | | | |
| Petrobras K 521 (A. Kochen Gmb) | 5.70 | 7.50 | 7.50 | 7.50 | 7.50 | 7.50 | 12.50 | 10.00 |
| Shell HMP (D. Shell AG) | | | | | | | | |
| Vestowax H2 TP 100C (Huls) | | | | | | | | |
| Sasol H4 (A. Kochen GmbH) | 9.30 | 12.50 | 12.50 | 12.50 | 12.50 | 12.50 | 12.50 | 10.00 |
| Eastotac R100H (Eastman) | 44.70 | 44.70 | 44.70 | 45.70 | 41.70 | 41.70 | 35.00 | 25.00 |
| Eastotac H130 (Eastman) | | | | | | | | |
| Wingtack 95 (Weber & Schaer) | | | | | | | | |
| Lacqtene 1200MN18C (Elf AtoChem) | | | | | | | | |
| PT 7007 (Dow) | | | | | | | | |
| LD780R (DOW) | | 5.00 | | | | | | 5.00 |
| LE Wachs 114 (Leuna-Werke GmbH) | | | | | | | | |
| TIO2 - preblend PE based (H. B. Fuller) | | | | | | | | |
| TIO2 - preblend EVA based (H. B. Fuller) | | | | | | | | |

TABLE III D-continued

| Tradename (Supplier) | 38 | 39 | 40 | 41 | 42 | 43 | 44 | 45 |
|---|---|---|---|---|---|---|---|---|
| Irganox 1010 FF (Ciba Additive GmbH) | 0.15 | 0.15 | 0.15 | 0.15 | 0.15 | 0.15 | 0.15 | 0.15 |
| Irganox PS800 (Ciba Additive GmbH) | 0.15 | 0.15 | 0.15 | 0.15 | 0.15 | 0.15 | 0.15 | 0.15 |

TABLE IV A

| Example | Nonwoven | Coating weight (g/m²) | Application Temp. (° C.) | Draw Resonance (at speed m/min) | Maschine speed (m/min) |
|---|---|---|---|---|---|
| 30 | Sandler 4326/outs. | 10,0 – 12,0 | 120 | | 100 |
| | Client (PT) | 12 | 140 | | 100 |
| | Client (PT) | 12 | 140 | | 100 |
| | Client (PT) | 8,0 – 10,0 | 140 | 222/5 mm | 222 |
| 35 | Corosoft Plus/ins | 9,0 – 10,0 | 140 | | 30 |
| | Fibertech/ins | 10,0 – 12,0 | 110 | | 30 |
| | Fibertech/ins | 10,0 – 12,0 | 120 | | 30 |
| 36 | Fibertech/ins | 11.0 | 130 | | 30 |
| 37 | Fibertech/ins | 11,0 – 12,0 | 140 | | 30 |
| | Fibertech/ins | 11,0 – 12,0 | 140 | | 30 |
| | Fibertech/ins | 12,4 ± 0,5 | 130 | | 30 |
| | Fibertech/ins | 12.0 | 120 | | 30 |
| | Fibertech/ins | 12.0 | 120 | | 30 |
| 38 | Fibertech/ins | 12 | 140 | 70 | 30 |
| | Corosoft Plus/ins | 11,0 – 12,0 | 140 | 70 | 30 |
| 39 | Fibertech/ins | 12,0 – 13,0 | 120 | | 30 |
| | Corosoft Plus/ins | 12,2 ± 0,7 | 120 | | 30 |
| | Corosoft Plus/ins | 9 | 120 | | 222 |
| 40 | Corosoft Plus/ins | 12,2 ± 0,3 | 120 | | 30 |
| | Corosoft Plus/ins | 7,7 ± 0,1 | 120 | | 222 |
| | Fibertech/ins | 12.0 | 120 | | 30 |
| | Fibertech/ins | 16.0 | 120 | | 30 |
| 41 | Corosoft Plus/ins | 12,0 – 13,0 | 120 | | 30 |
| | Corosoft Plus/ins | 11,5 ± 0,4 | 120 | | 222 |
| | Client (PT) | 12,5 ± 0,5 | 120 | | 100 |
| | Client (PT) | 11,9 ± 0,3 | 140 | | 100 |
| 42 | Corosoft Plus/ins | | 120 | 100/2 mm | 30/100 |
| | Corosoft Plus/ins | | 140 | 30/2 mm | 30 |
| 43 | Corosoft Plus/ins | 11 | 120 | | 30 |
| | Corosoft Plus/ins | 6 | 120 | 222/5 mm | 222 |
| 44 | Corosoft Plus/ins | | 120 | | 30 |
| | Corosoft Plus/ins | 16 | 120 | | 222 |
| | Corosoft Plus/ins | 19 | 100 | | 30 |
| | Corosoft Plus/ins | 7 | 100 | 222/5 mm | 222 |
| 45 | Corosoft Plus/ins | | 140 | 30/10 mm | 30 |
| | Corosoft Plus/ins | 10,5 ± 0,7 | 120 | slight reso | 30 |
| | Corosoft Plus/ins | 5 | 120 | 222/2 mm | 222 |

TABLE IV B

| Example | initial 23° C. | Water resi 1–4d 23° C. | Nonwoven | tence (cm) 3d/ 38° C. | 3d/ 60° C. |
|---|---|---|---|---|---|
| 30 | 60 | | Sandler 4326/outs. | | |
| | 130 | 120 | Client (PT) | 130 | 120 |
| | 180 | | Client (PT) | | |
| | | | Client (PT) | | |
| 35 | 50 | | Corosoft Plus/ins | | |
| | 80 | | Fibertech/ins | | |
| | 70 | | Fibertech/ins | | |
| 36 | 20 | | Fibertech/ins | | |
| 37 | 50 | | Fibertech/ins | | |
| | 60 | | Fibertech/ins | | |
| | 90 | 60 | Fibertech/ins | 50 | 40 |
| | 80 | | Fibertech/ins | | |
| | 70 | | Fibertech/ins | | |
| 38 | 40 | | Fibertech/ins | | |
| | 150 | | Corosoft Plus/ins | | |
| 39 | 60 | | Fibertech/ins | | |
| | 180 | 120 | Corosoft Plus/ins | 100 | 90 |
| | 130 | 40 | Corosoft Plus/ins | 40 | 30 |
| 40 | 280 | 210 | Corosoft Plus/ins | 150 | 190 |
| | 150 | 50 | Corosoft Plus/ins | 40 | 10 |
| | 60 | | Fibertech/ins | | |
| | 60 | | Fibertech/ins | | |
| 41 | 300 l | | Corosoft Plus/ins | | |
| | 180 | 170 | Corosoft Plus/ins | 130 | 50 |
| | 70 | 90 | Client (PT) | 60 | 70 |
| | 130 | 80 | Client (PT) | 80 | 60 |
| 42 | | | Corosoft Plus/ins | | |
| | | | Corosoft Plus/ins | | |
| 43 | 80 | | Corosoft Plus/ins | | |
| | 20 | | Corosoft Plus/ins | | |
| 44 | | | Corosoft Plus/ins | | |
| | 100 | | Corosoft Plus/ins | | |
| | 140 | | Corosoft Plus/ins | | |

TABLE IV B-continued

| Example | initial 23° C. | Water resi 1–4d 23° C. | Nonwoven | tence (cm) 3d/ 38° C. | 3d/ 60° C. |
|---|---|---|---|---|---|
| 45 |  |  | Corosoft Plus/ins |  |  |
|  | 260 | 90 | Corosoft Plus/ins | 150 | 160 |
|  |  |  | Corosoft Plus/ins |  |  |

What is claimed is:

1. A disposable article comprising at least one permeable substrate layer and at least one fluid impermeable barrier layer substantially adhered to the permeable substrate layer on at least one face, wherein said barrier layer comprises a thermoplastic coating composition comprising up to 100 weight percent of at least one interpolymer which is a homogeneous linear or substantially linear interpolymer of ethylene with at least one $C_3$–$C_{20}$ alpha-olefin, said interpolymer being characterized as having a polydispersity less than about 2.5 and a density from 0.850 to 0.965 g/cc and wherein the complex viscosity of the thermoplastic coating composition at a temperature less than 160° C. is less than about 500 poise at about 1,000 radian/sec and ranges from about 100 to about 1,000 poise at about 1 radian/sec, said coating composition is dispensed from a coating device as a continuous film at a temperature less than 160° C. and said coating device is spaced from the substrate at a distance between about 0.5 to about 20 mm.

2. A disposable article comprising at least one permeable substrate layer and at least one fluid impermeable barrier layer substantially adhered to the permeable substrate layer on at least one face, wherein said barrier layer comprises a hot melt adhesive comprising:
   a) from about 10 to about 60 wt-% of at least one interpolymer which is a homogeneous linear or substantially linear interpolymer of ethylene with at least one $C_3$–$C_{20}$ alpha-olefin, said interpolymer being characterized as having a polydispersity less than about 2.5 and a density from 0.850 to 0.900 g/cc;
   b) from about 40 to about 90 wt-% of at least one viscosity reducing agent selected from the group consisting of tackifier, plasticizer, wax, oils, and mixtures thereof.

3. The article of claim 2, wherein the area weight of said barrier layer is less than about 30 g/m².

4. The disposable article of claim 2, wherein the article further comprises at least one absorbent material.

5. The disposable article of claim 2, wherein the permeable substrate layer is a textile material.

6. A disposable article comprising at least one permeable substrate layer and at least one fluid impermeable barrier layer substantially adhered to the permeable substrate layer on at least one face, wherein said barrier layer comprises a thermoplastic composition comprising up to 100 weight percent of at least one interpolymer which is a homogeneous linear or substantially linear interpolymer of ethylene with at least one $C_3$–$C_{20}$ alpha-olefin, said interpolymer being characterized as having a polydispersity less than about 2.5 and a density from 0.850 to 0.965 g/cc, and wherein the complex viscosity of the thermoplastic composition at coating temperature is less than about 500 poise at about 1,000 radians/sec.

7. The article of claim 6, wherein the coating temperature is less than about 160° C.

8. The article of claim 6, wherein the thermoplastic composition forming the barrier layer is subsequently bonded to at least one other material.

9. The article of claim 6, wherein the thermoplastic composition is bonded to at least one other material inline after coating of the thermoplastic composition.

10. The article of claim 6, wherein the area weight of the thermoplastic composition is less than about 20 g/m².

11. The article of claim 6, wherein the area weight of the thermoplastic composition is less than about 10 g/m².

12. A disposable article comprising at least one permeable substrate layer and at least one fluid impermeable barrier layer substantially adhered to the permeable substrate layer on at least one face, wherein said barrier layer comprises a thermoplastic coating composition comprising up to 100 weight percent of at least one interpolymer which is a homogeneous linear or substantially linear interpolymer of ethylene with at least one $C_3$–$C_{20}$ alpha-olefin, said interpolymer being characterized as having a polydispersity less than about 2.5 and a density from 0.850 to 0.965 g/cc, and wherein the complex viscosity of the thermoplastic composition at coating temperature ranges from about 100 poise to about 1,000 poise at about 1 radian/sec.

13. The article of claim 12, wherein the coating temperature is less than about 160° C.

14. The article of claim 12, wherein the thermoplastic composition forming the barrier layer is subsequently bonded to at least one other material.

15. The article of claim 12, wherein the thermoplastic composition is bonded to at least one other material inline after coating of the thermoplastic composition.

16. The article of claim 12, wherein the area weight of the thermoplastic composition is less than about 20 g/m².

17. The article of claim 12, wherein the area weight of the thermoplastic composition is less than about 10 g/m².

18. The article of claim 9 wherein the at least one interpolymer has a density of less than about 0.890 g/cc, and a melt index of less than about 1 g/10 min. and said thermoplastic composition further comprises a viscosity reducing agent.

19. The article of claim 6 wherein the thermoplastic composition has a tan delta of less than about 50 at 0.1 radians/sec.

20. The article of claim 15 wherein the at least one interpolymer has a density of less than about 0.890 g/cc, and a melt index of less than about 1 g/10 min. and said thermoplastic composition further comprises a viscosity reducing agent.

21. The article of claim 12 wherein the thermoplastic composition has a tan delta of less than about 50 at 0.1 radians/sec.

22. An article comprising at least one substrate layer and at least one thermoplastic coating substantially adhered to the substrate layer on at least one face, wherein said thermoplastic coating comprises up to 100 weight percent of at least one interpolymer which is a homogeneous linear or substantially linear interpolymer of ethylene with at least one $C_3$–$C_{20}$ alpha-olefin, said interpolymer being characterized as having a polydispersity less than about 2.5 and a density from 0.850 to 0.965 g/cc, and wherein the complex viscosity of the thermoplastic coating at coating temperature is less than about 500 poise at about 1,000 radians/sec.

23. An article comprising at least one substrate layer and at least one thermoplastic coating substantially adhered to the substrate layer on at least one face, wherein said thermoplastic coating comprises up to 100 weight percent of at least one interpolymer which is a homogeneous linear or substantially linear interpolymer of ethylene with at least one $C_3$–$C_{20}$ alpha-olefin, said interpolymer being characterized as having a polydispersity less than about 2.5 and a density from 0.850 to 0.965 g/cc, and wherein the complex viscosity of the thermoplastic composition at coating temperature ranges from about 100 poise to about 1,000 poise at about 1 radian/sec.

24. The article of claim 22, wherein the coating temperature is less than about 160° C.

25. The article of claim 23, wherein the coating temperature is less than about 160° C.

* * * * *